US009770596B2

(12) United States Patent
Nassif et al.

(10) Patent No.: US 9,770,596 B2
(45) Date of Patent: *Sep. 26, 2017

(54) ANTENNA AND METHODS OF USE FOR AN IMPLANTABLE NERVE STIMULATOR

(71) Applicant: Axonics Modulation Technologies, Inc., Irvine, CA (US)

(72) Inventors: Rabih Nassif, Santa Ana, CA (US); Hisham Hasbini, Laguna Niguel, CA (US)

(73) Assignee: AXONICS MODULATION TECHNOLOGIES, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,745

(22) Filed: Jan. 17, 2017

(65) Prior Publication Data
US 2017/0120061 A1    May 4, 2017

Related U.S. Application Data

(63) Continuation of application No. 14/993,009, filed on Jan. 11, 2016, now Pat. No. 9,700,731.
(Continued)

(51) Int. Cl.
*A61N 1/08* (2006.01)
*A61N 1/372* (2006.01)
(Continued)

(52) U.S. Cl.
CPC ..... *A61N 1/37229* (2013.01); *A61N 1/36125* (2013.01); *A61N 1/3787* (2013.01);
(Continued)

(58) Field of Classification Search
CPC ............ A61N 1/37229; A61N 1/36125; A61N 1/37235; A61N 1/3787; H04B 1/40;
(Continued)

(56) References Cited

U.S. PATENT DOCUMENTS 3,646,940 A    3/1972  Timm et al.
4,019,518 A    4/1977  Maurer et al.
(Continued)

FOREIGN PATENT DOCUMENTS

EP    1680182 A1    7/2006
EP    1680182 B1    7/2006
(Continued)

OTHER PUBLICATIONS

Claims from U.S. Appl. No. 14/993,009, filed Jan. 11, 2016.*
(Continued)

*Primary Examiner* — Michael Carey
(74) *Attorney, Agent, or Firm* — Kilpatrick Townsend & Stockton LLP

(57) ABSTRACT

A pulse generator that includes a communications module is disclosed herein. The communication module includes a transceiver and an antenna circuit. The antenna circuit includes a first pathway having a capacitor and a second, parallel pathway including a capacitor, and a resistor, and a radiating element arranged in series. The antenna circuit is tuned to have a resonant frequency corresponding to a desired transmission frequency and a bandwidth corresponding to shifts in the resonant frequency arising from the implantation of the antenna.

20 Claims, 15 Drawing Sheets

Related U.S. Application Data

(60) Provisional application No. 62/101,782, filed on Jan. 9, 2015.

(51) Int. Cl.
*A61N 1/378* (2006.01)
*A61N 1/36* (2006.01)
*H04B 1/3827* (2015.01)
*H01Q 1/38* (2006.01)
*H01Q 7/08* (2006.01)

(52) U.S. Cl.
CPC .......... *A61N 1/37235* (2013.01); *H01Q 1/38* (2013.01); *H01Q 7/08* (2013.01); *H04B 1/385* (2013.01)

(58) Field of Classification Search
CPC ..... H04B 1/385; H04W 72/0453; H01Q 1/38; H01Q 7/08
USPC .................................. 607/2, 60, 61, 65, 116
See application file for complete search history.

(56) References Cited

U.S. PATENT DOCUMENTS

| | | |
|---|---|---|
| 4,044,774 A | 8/1977 | Corbin et al. |
| 4,340,062 A | 7/1982 | Thompson et al. |
| 4,558,702 A | 12/1985 | Barreras et al. |
| 4,744,371 A | 5/1988 | Harris |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 5,951,594 A | 9/1999 | Kerver |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,172,556 B1 | 1/2001 | Prentice |
| 6,178,353 B1 | 1/2001 | Griffith et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,456,256 B1 | 9/2002 | Amundson et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,614,406 B2 | 9/2003 | Amundson et al. |
| 6,652,449 B1 | 11/2003 | Gross et al. |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,931,284 B2 | 8/2005 | Engmark et al. |
| 6,941,171 B2 | 9/2005 | Mann et al. |
| 6,971,393 B1 | 12/2005 | Mamo et al. |
| 6,972,543 B1 | 12/2005 | Wells |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,149,578 B2 | 12/2006 | Edvardsson |
| 7,151,914 B2 | 12/2006 | Brewer |
| 7,167,749 B2 | 1/2007 | Biggs et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,245,972 B2 | 7/2007 | Davis |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,326,181 B2 | 2/2008 | Katims |
| 7,328,068 B2 | 2/2008 | Spinelli et al. |
| 7,330,764 B2 | 2/2008 | Swoyer et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,496,404 B2 | 2/2009 | Meadows et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,613,522 B2 | 11/2009 | Christman et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,706,889 B2 | 4/2010 | Gerber et al. |
| 7,720,544 B2 | 5/2010 | Christman et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |

(56) References Cited

U.S. PATENT DOCUMENTS

| | | |
|---|---|---|
| 7,848,818 B2 | 12/2010 | Barolat et al. |
| 7,904,167 B2 | 3/2011 | Klosterman et al. |
| 7,908,014 B2 | 3/2011 | Schulman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,953,493 B2 | 5/2011 | Fowler et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,050,771 B2 | 11/2011 | Yamamoto et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,229,567 B2 | 7/2012 | Phillips et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,352,044 B2 | 1/2013 | Christman et al. |
| 8,362,742 B2 | 1/2013 | Kallmyer |
| 8,369,943 B2 | 2/2013 | Shuros et al. |
| 8,369,961 B2 | 2/2013 | Christman et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,497,804 B2 | 7/2013 | Haubrich et al. |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,565,891 B2 | 10/2013 | Mumbru et al. |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,061,159 B2 | 6/2015 | Rahman |
| 9,089,712 B2 | 7/2015 | Joshi et al. |
| 9,108,063 B2 | 8/2015 | Olson et al. |
| 2005/0104577 A1 | 5/2005 | Matei et al. |
| 2005/0222633 A1 | 10/2005 | Edvardsson |
| 2006/0142822 A1 | 6/2006 | Tulgar |
| 2006/0206166 A1 | 9/2006 | Weiner |
| 2007/0265675 A1 | 11/2007 | Lund et al. |
| 2007/0293914 A1 | 12/2007 | Woods et al. |
| 2008/0183236 A1 | 7/2008 | Gerber |
| 2009/0030488 A1 | 1/2009 | Bruinsma |
| 2009/0192574 A1 | 7/2009 | Von Arx et al. |
| 2009/0259265 A1 | 10/2009 | Stevenson et al. |
| 2010/0076254 A1 | 3/2010 | Jimenez et al. |
| 2010/0076534 A1 | 3/2010 | Mock |
| 2010/0109966 A1 | 5/2010 | Mateychuk et al. |
| 2010/0185263 A1* | 7/2010 | Stevenson ............ A61B 5/0031 607/60 |
| 2011/0022140 A1 | 1/2011 | Stevenson et al. |
| 2011/0137378 A1 | 6/2011 | Klosterman et al. |
| 2011/0282416 A1 | 11/2011 | Hamann et al. |
| 2011/0288615 A1* | 11/2011 | Armstrong ........... A61B 5/0031 607/59 |
| 2011/0301667 A1 | 12/2011 | Olson et al. |
| 2012/0041512 A1 | 2/2012 | Weiner |
| 2012/0046712 A1 | 2/2012 | Woods et al. |
| 2012/0130448 A1 | 5/2012 | Woods et al. |
| 2012/0203082 A1 | 8/2012 | Livneh et al. |
| 2012/0249383 A1 | 10/2012 | Hsu et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0150925 A1 | 6/2013 | Vamos et al. |
| 2013/0197608 A1 | 8/2013 | Eiger |
| 2013/0207863 A1 | 8/2013 | Joshi |
| 2013/0274829 A1 | 10/2013 | Gupta et al. |
| 2013/0310894 A1 | 11/2013 | Trier |
| 2013/0331909 A1 | 12/2013 | Gerber |
| 2014/0031903 A1 | 1/2014 | Maschiach |
| 2014/0207220 A1* | 7/2014 | Boling ................. A61N 1/0546 607/116 |
| 2014/0222112 A1 | 8/2014 | Fell |
| 2014/0237806 A1 | 8/2014 | Smith et al. |
| 2014/0277260 A1 | 9/2014 | Khalil et al. |
| 2014/0277270 A1 | 9/2014 | Parramon et al. |
| 2015/0214604 A1 | 7/2015 | Zhao et al. |

FOREIGN PATENT DOCUMENTS

| | | |
|---|---|---|
| EP | 1904153 B1 | 4/2008 |
| EP | 2243509 A1 | 10/2010 |
| WO | WO 00/56677 A1 | 3/2000 |
| WO | WO 2004/002572 A1 | 1/2004 |
| WO | WO 2005/115540 A1 | 12/2005 |
| WO | WO 2006/131302 A1 | 12/2006 |
| WO | WO 2008/021524 A2 | 2/2008 |
| WO | WO 2009/086405 A2 | 7/2009 |
| WO | WO 2010/051189 A1 | 5/2010 |
| WO | WO 2010/051249 A1 | 5/2010 |
| WO | WO 2010/056751 A1 | 5/2010 |
| WO | WO 2010/077897 A1 | 7/2010 |

(56) References Cited

FOREIGN PATENT DOCUMENTS

| WO | WO 2011/039752 A2 | 4/2011 |
|---|---|---|
| WO | WO 2011/059564 A1 | 5/2011 |
| WO | WO 2011/059565 A1 | 5/2011 |
| WO | WO 2011/060160 A1 | 5/2011 |
| WO | WO 2011/073334 A1 | 6/2011 |
| WO | WO 2013/141884 A2 | 9/2013 |
| WO | WO 2013/158667 A1 | 10/2013 |

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Tanagho, E., et al., Bladder Pacemaker: Scientific Basis and Clinical Future, Urology, Dec. 1982, vol. 20, No. 6, pp. 614-619.

Minco Bulletin FC-1, "Minco: Flex-Coils", Minco Products, Inc., Sep. 2001, Serial 850614-1, pp. 1-4.

U.S. Appl. No. 62/101,888, filed Jan. 9, 2015.
U.S. Appl. No. 62/101,899, filed Jan. 9, 2015.
U.S. Appl. No. 62/041,611, filed Aug. 25, 2014.
U.S. Appl. No. 62/038,131, filed Aug. 15, 2014.
U.S. Appl. No. 62/101,897, filed Jan. 9, 2015.
U.S. Appl. No. 62/038,122, filed Aug. 15, 2014.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.

* cited by examiner

ANTENNA AND METHODS OF USE FOR AN IMPLANTABLE NERVE STIMULATOR

CROSS-REFERENCES TO RELATED APPLICATIONS

The present application is a continuation of U.S. application Ser. No. 14/993,009, filed on Jan. 11, 2016, and entitled "Improved Antenna and Methods of use for an Implantable Nerve Stimulator," which is a non-provisional of and claims the benefit of priority of U.S. Provisional Application No. 62/101,782 filed on Jan. 9, 2015, and entitled "Improved Antenna and Methods of use for an Implantable Nerve Stimulator," the entirety of each of which is hereby incorporated by reference herein. The present application is related to U.S. Provisional Patent Application Nos. 62/038,122 filed on Aug. 15, 2014 and entitled "Devices and Methods for Anchoring of Neurostimulation Leads"; 62/038,131, filed on Aug. 15, 2014 and entitled "External Pulse Generator Device and Associated Methods for Trial Nerve Stimulation"; 62/041,611, filed on Aug. 25, 2014 and entitled "Electromyographic Lead Positioning and Stimulation Titration in a Nerve Stimulation System for Treatment of Overactive Bladder, Pain and Other Indicators"; U.S. Provisional Patent Application No. 62/101,888, filed on Jan. 9, 2015 and entitled "Electromyographic Lead Positioning and Stimulation Titration in a Nerve Stimulation System for Treatment of Overactive Bladder", U.S. Provisional Patent Application No. 62/101,899, filed on Jan. 9, 2015 and entitled "Integrated Electromyographic Clinician Programmer For Use With an Implantable Neurostimulator;" U.S. Provisional Patent Application No. 62/101,897, filed on Jan. 9, 2015 and entitled "Systems and Methods for Neurostimulation Electrode Configurations Based on Neural Localization;" U.S. Provisional Patent Application No. 62/101,666, filed on Jan. 9, 2015 and entitled "Patient Remote and Associated Methods of Use With a Nerve Stimulation System;" and U.S. Provisional Patent Application No. 62/101,884, filed on Jan. 9, 2015 and entitled "Attachment Devices and Associated Methods of Use With a Nerve Stimulation Charging Device"; each of which is assigned to the same assignee and incorporated herein by reference in its entirety for all purposes.

FIELD OF THE INVENTION

The present invention relates to neurostimulation treatment systems and associated devices, as well as methods of treatment, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, frequency, and/ or voltage that is effective to affect a body function for one patent may impose significant pain on, or have limited effect for, another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, current stimulation systems rely on wireless communication to maintain control of the implantable neurostimulation system. This wireless communication is frequently performed using one or more antennas. However, current antennas do not perform well under certain circumstances, and particularly when the antenna is implanted within the body of a patient. This leads to decreased ability to communicate with implanted devices and difficulty in maintaining control of those devices.

The tremendous benefits of these neural stimulation therapies have not yet been fully realized. Therefore, it is desirable to provide improved neurostimulation methods, systems and devices, as well as methods for implanting and configuring such neurostimulation systems for a particular patient or condition being treated. It would be particularly helpful to provide such systems and methods so as to improve ease of use by the physician in implanting and configuring the system, as well as to improve patient comfort and alleviation of symptoms for the patient, and/or to provide a redesigned antenna to improve communications with the implanted antenna.

BRIEF SUMMARY OF THE INVENTION

One aspect of the present disclosure relates to a communication module that includes a transceiver and an antenna circuit. The antenna circuit can have a first resonant frequency when the antenna circuit is not implanted in a patient's body, a second resonant frequency when the antenna circuit is implanted in the patient's body, and a bandwidth. The bandwidth of the antenna circuit can be sufficient that a transmission frequency is received at the antenna circuit at greater than the half-power point when the antenna circuit is in vivo, despite variability imposed on the resonant frequency of the transmission system. As the shift from the first resonant frequency to the second resonant frequency varies from patient to patient based on implantation and/or tissue properties of the patient, such a bandwidth of the antenna circuit enables effective communication between implanted and external devices without custom tuning of the antenna circuit for a specific implantation in a specific patient.

One aspect of the present disclosure relates to an implantable neurostimulator for delivering one or more electrical pulses to a target region within a patient's body according to a program received via wireless communication with an external device. The implantable neurostimulator can include a hermetic housing having an external surface comprising a biocompatible material that can be implanted within a body of a patient, a transceiver disposed within the housing and including a first lead and a second lead, and a communication antenna circuit disposed within the housing and coupled to the first lead and the second lead, the antenna circuit having a first path and a second path parallel to the first path. In some embodiments, the first path includes a first capacitor, and the second path includes a second capacitor, a radiating element, and a resistor, wherein the second capacitor, the resistor, and the radiating element are arranged in series.

In some embodiments, the antenna circuit includes a printed circuit board (PCB), and in some embodiments, the radiating element can include a plurality of conductive loops of the PCB, which plurality of conductive loops can be located along and/or within a common plane of the PCB. In some embodiments, the conductive loops can include copper traces embedded onto a substrate surface of the PCB, which copper traces can produce an electric field dipole having a donut pattern with a maximum strength in the common plane, and which maximum field is substantially normal to a body surface of the patient when the housing is implanted. In some embodiments, the plurality of loops include a first loop and a second loop, which second loop can be located within the first loop.

In some embodiments of the implantable neurostimulator, the antenna circuit has a fixed natural resonant frequency, the first capacitor has a first fixed capacitance and the second capacitor has a second fixed capacitance. In some embodiments, the antenna circuit is defined by a Q factor and the resistor is configured to diminish the Q factor of the antenna circuit. In some embodiments, the housing includes at least a ceramic case portion so as to provide an efficient radio frequency transparent window for wireless communication between the implantable neurostimulator and the external device, which the external device can include a clinician programmer, patient remote, or a charging device.

One aspect of the present disclosure relates to an implantable neurostimulator for delivering one or more electrical pulses to a target region within a patient's body. The implantable neurostimulator includes a hermetic and at least partially ceramic housing having an external surface that can be implanted within a body of a patient, an antenna circuit defined by a Q factor disposed within the housing and that can wirelessly communicate with an external device, and a transceiver disposed within the housing and coupled to the antenna circuit. In some embodiments, the Q factor of the antenna circuit is limited or diminished at a target frequency by a first resistor included in the antenna circuit.

In some embodiments, the first resistor increases a bandwidth of the antenna circuit. In some embodiments, the target frequency is between 350 and 450 Hz, and in some embodiments, the target frequency is approximately 403 Hz. In some embodiments, the second resistor is selected so that the bandwidth of the antenna circuit is between 5 Hz and 30 Hz, such bandwidth often being greater than 10 Hz or even 15 Hz, and in some embodiments, the bandwidth of the antenna circuit is approximately 16 Hz.

In some embodiments, the antenna circuit includes a first capacitor arranged in parallel with a second capacitor, a radiating element, and the first resistor. In some embodiments, the antenna circuit includes a printed circuit board (PCB), the radiating element includes a plurality of conductive loops on a surface of a substrate of the PCB, and the plurality of conductive loops are located within a common plane on the PCB. In some embodiments, the plurality of loops includes a first loop and a second loop, which second loop is located within the first loop. In some embodiments, the first capacitor has a first fixed capacitance, and the second capacitor has a second fixed capacitance.

One aspect of the present disclosure relates to an implantable neurostimulator for delivering one or more electrical pulses to a target region within a patient's body. The implantable neurostimulator includes an at least partially ceramic housing having an external surface that can be implanted within a body of a patient, a radio frequency transceiver disposed within the ceramic housing and having a first lead and a second lead, and an antenna circuit disposed within the ceramic housing and configured to wirelessly communicate with an external device, the antenna circuit coupled to the first lead and the second lead and having a first path and a second path parallel to the first path. In some embodiments, the first path includes a first capacitor and the second path includes a resonant tuned (RLC) circuit. In some embodiments, the antenna circuit has a fixed resonant frequency.

In some embodiments, the antenna circuit includes a printed circuit board (PCB), and in some embodiments, the radiating element includes a plurality of conductive loops formed on the PCB, which plurality of loops include a first loop, and a second loop, which second loop is located within the first loop. In some embodiments, the fixed resonant frequency corresponds to a transmitting frequency at which the implantable neurostimulator can receive one or more wireless communications.

In some embodiments, the antenna circuit has a bandwidth, which bandwidth of the antenna circuit is tuned such that an effectiveness of the antenna circuit at receiving the transmitting frequency does not drop below a half-power point of the antenna when implanted within the body of the patient.

One aspect of the present disclosure relates to a method of wireless communication of data between an implantable neurostimulator and an external device. The method includes implanting the neurostimulator with a patient's body, which implantable neurostimulator can include a hermetic housing, a transceiver disposed within the housing, which transceiver can include a first lead and a second lead, and an antenna circuit disposed within the housing and coupleable to the first lead and the second lead. In some embodiments, the antenna circuit can have a first path and a second path parallel to the first path, which first path can include a first capacitor, and which second path can include a second capacitor, a radiating element, and a resistor. In some embodiments, the second capacitor, the resistor, and the radiating element are arranged in series, and the antenna circuit has a resonant frequency. In some embodiments, the method can include receiving data wirelessly transmitted from the external device at the implantable neurostimulator, which data is transmitted at a transmission frequency and can control delivery of one or more electrical pulses to a target region within the patient's body.

In some embodiments of the method, implanting the neurostimulator into the patient's body creates an effective resonant frequency of the antenna circuit based on one or more properties of a tissue of the patient's body into which the neurostimulator is implanted. In some embodiments, the one or more properties of a tissue of the patient's body can include at least one of: a density, a hydration level, a resistance, an inductance, and a tissue type. In some embodiments, the antenna circuit can be tuned to have a bandwidth encompassing both the effective resonant frequency and the transmission frequency.

In some embodiments, the antenna circuit can include a printed circuit board (PCB), and in some embodiments, the radiating element can be a plurality of conductive loops formed on the PCB. In some embodiments, the plurality of loops include a first loop, and second loop, which second loop can be located within the first loop.

One aspect of the present disclosure relates to a method of manufacturing a communication module for an implantable neurostimulator for wireless data communication from within a patient's body and an external device. The method includes selecting a transceiver, and connecting the transceiver to an antenna circuit. In some embodiments, the antenna circuit can have a first resonant frequency when not implanted in a patient's body, and a second resonant frequency when implanted in a patient's body. In some embodiments, the second resonant frequency varies from patient to patient based on one or more tissue characteristics (type of tissue, tissue thickness, etc.) of the patient, the implant characteristics (location, depth, etc.), and/or the like. In some embodiments, the antenna circuit can have a first path and a second path parallel to the first path, the first path including a first capacitor, and the second path including a second capacitor, a radiating element, and a resistor. In some embodiments, the resistor increases the bandwidth of the antenna circuit such that the bandwidth includes the transmission frequency when the antenna is implanted in the patient's body.

In some embodiments, the bandwidth is between 5 Hz and 30 Hz, and in some embodiments, the bandwidth is approximately 16 Hz. In some embodiments, the antenna circuit includes a printed circuit board. In some embodiments, the radiating element includes a plurality of loops printed on the printed circuit board, which plurality of loops includes a first loop and a second loop positioned within the first loop. In some embodiments, the first capacitor has a first fixed capacitance and the second capacitor has a second fixed capacitance One aspect of the present disclosure relates to a method of wireless communication of data between an implantable neurostimulator and an external device. The method includes implanting the neurostimulator within a patient's body, the neurostimulator including an antenna circuit disposed within a housing and having a first path and a second path parallel to the first path. In some embodiments, the first path can include a first capacitor, the second path can include a second capacitor, a radiating element, and a resistor, which second capacitor, resistor, and radiating element are arranged in series such that the antenna circuit has a first resonant frequency prior to implantation. In some embodiments, the antenna circuit and the external device together have a second resonant frequency differing from the first resonant frequency after implantation, the second resonant frequency being within an implanted resonant frequency range encompassing patient-to-patient resonant frequency variability. In some embodiments, the method can include transmitting data wirelessly between the external device and the implantable neurostimulator, which data is transmitted at a transmission frequency corresponding to the second resonant frequency. In some embodiments, the second resistor is sufficient to maintain the wireless data transmission above a half-power point of the antenna circuit throughout the implanted resonant frequency range.

One aspect of the present disclosure relates to a neurostimulation system for delivering one or more electrical pulses to a target region within a patient's body. The neurostimulation system includes: a neurostimulator and a charger. The neurostimulator can include a hermetic housing having an external surface. The housing can be implantable within a body of a patient, and the housing can include a ceramic transmission region. The neurostimulator can include: a first antenna circuit positioned to wirelessly communicate with an external device through the ceramic region; and a transceiver disposed within the housing and coupled to the first antenna circuit. The charger can include a second antenna circuit having a first path and a second path parallel to the first path. The first path can include a first capacitor, and the second path can include: a second capacitor; a radiating element; and a resistor. In some embodiments, the second capacitor, the resistor, and the radiating element are arranged in series.

In some embodiments, both of the first antenna circuit and the second antenna circuits comprise printed circuit boards (PCB). In some embodiments, at least one of the first radiating element or the second radiating includes a plurality of conductive loops on the PCB, which plurality of conductive loops are located along a common plane of the PCB. In some embodiments, the conductive loops include copper traces embedded onto a substrate surface of the PCB/. In some embodiments, the copper traces can be laid-out to produce an electric field dipole having a donut pattern with a maximum strength in the common plane such that a maximum field is substantially normal to a body surface of the patient when the housing is implanted for use.

In some embodiments, the plurality of loops includes a first loop and a second loop, which second loop is located within the first loop. In some embodiments, the antenna circuit has a fixed natural resonant frequency, the first capacitor has a first fixed capacitance and the second capacitor has a second fixed capacitance. In some embodiments, the antenna circuit is defined by a Q factor and the resistor is selected to diminish the Q factor of the antenna circuit such that a bandwidth of the antenna circuits encompasses patient implantation-related variability in resonant frequency when the antenna circuit is implanted in the patient body and communicates with the external device.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Figure 1:
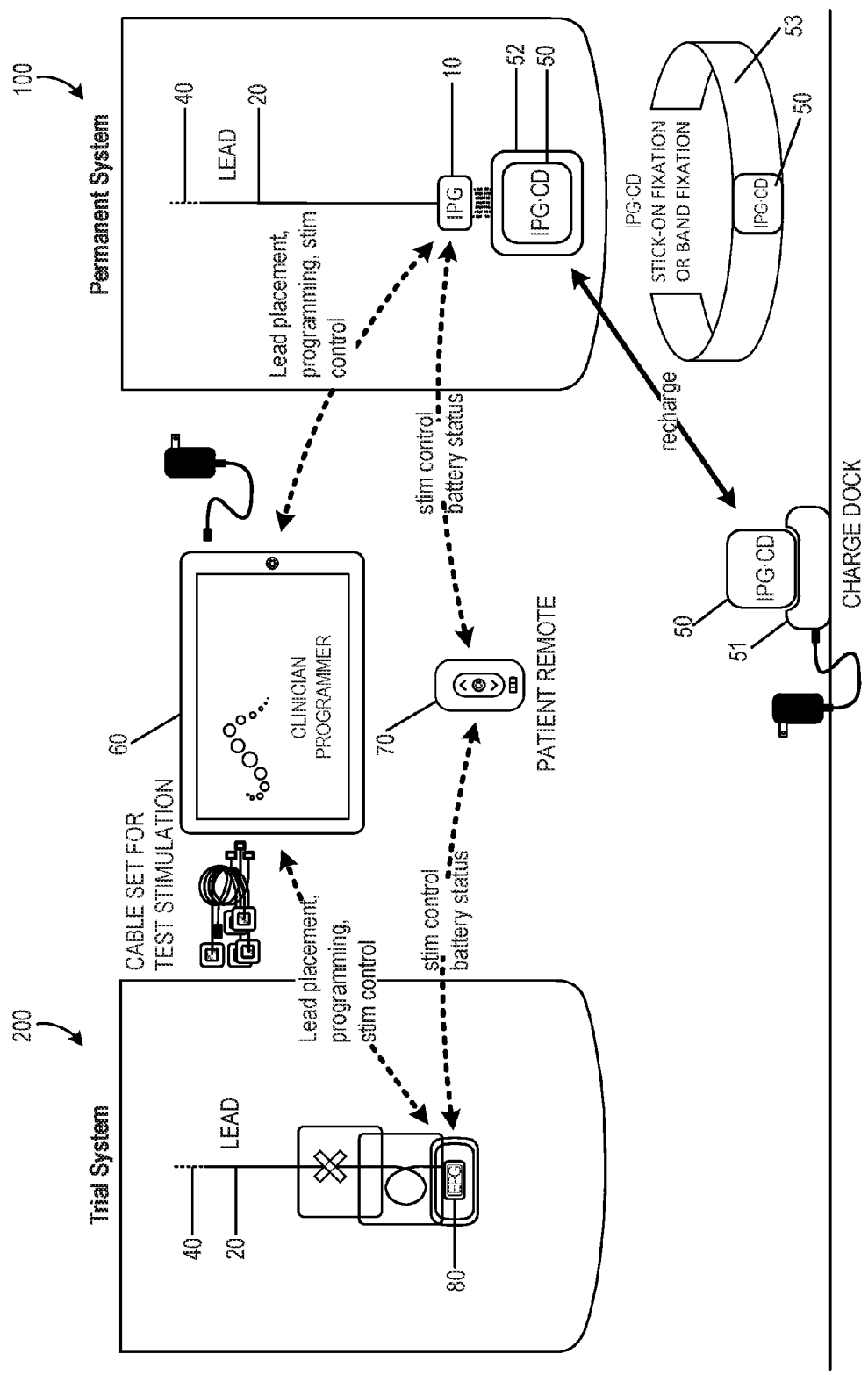
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In one particular embodiment, the invention relates to sacral nerve stimulation treatment systems configured to treat overactive bladder ("OAB") and relieve symptoms of bladder related dysfunction. It will be appreciated however that the present invention may also be utilized for any variety of neuromodulation uses, such as fecal dysfunction, the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of Botulinum Toxin (BoNT-A), Percutaneous Tibial Nerve Stimulation (PINS) and Sacral Nerve Stimulation (SNM). BoNT-A (Botox®) is administered via a series of intradetrusor injections under cystoscopic guidance, but repeat injections of BoNT-A are generally required every 4 to 12 months to maintain effect and BoNT-A may undesirably result in urinary retention. A number or randomized controlled studies have shown some efficacy of BoNT-A in OAB patients, but long-term safety and effectiveness of BoNT-A for OAB is largely unknown.

Alternative treatment methods, typically considered when the above approaches prove ineffective, is neurostimulation of nerves relating to the urinary system. Such neurostimulation methods include PINS and SNM. PINS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PINS has been demonstrated in a few randomized-controlled studies, however, long-term safety and effectiveness of PINS is relatively unknown at this time.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
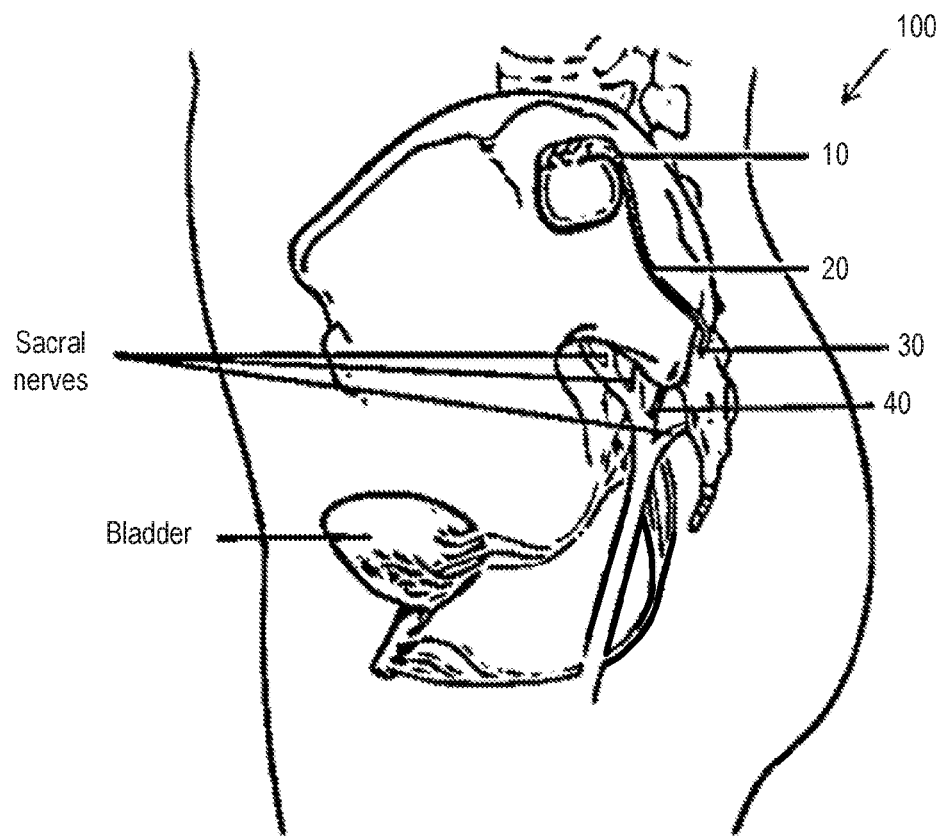
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

TABLE 1

Motor and Sensory Responses of SNM at Different Sacral Nerve Roots

| | | Response | | |
|---|---|---|---|---|
| | Nerve Innervation | Pelvic Floor | Foot/calf/leg | Sensation |
| S2 | Primary somatic contributor of pudendal nerve for external sphincter, leg, foot | "clamp"* of anal sphincter | Leg/hip rotation, plantar flexion of entire foot, contraction of calf | Contraction of base of penis, vagina |
| S3 | Virtually all pelvic autonomic functions and striated muscle (levator ani) | "bellows"** of perineum | Plantar flexion of great toe, occasionally other toes | Pulling in rectum, extending forward to scrotum or labia |
| S4 | Pelvic autonomic and somatic No leg or foot | "bellows"** | No lower extremity motor stimulation | Pulling in rectum only |

*Clamp: contraction of anal sphincter and, in males, retraction of base of penis. Move buttocks aside and look for anterior/posterior shortening of the perineal structures.
**Bellows: lifting and dropping of pelvic floor. Look for deepening and flattening of buttocks groove.

In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupt, inhibit, or prevent neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

B. Positioning Neurostimulation Leads with EMG

While conventional approaches have shown efficacy in treatment of bladder related dysfunction, there exists a need to improve positioning of the neurostimulation leads and consistency between the trial and permanent implantation positions of the lead. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measureable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measureable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example Embodiments

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the clinician programmer may be configured for coupling with an electrical ground or ground patch, an electrical pulse generator (e.g., an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG during test simulation through a specialized cable set. The test simulation cable set can connect the clinician programmer device to the EPG and allow the clinician programmer to configure, modify, or otherwise program the electrodes on the leads connected to the EPG.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
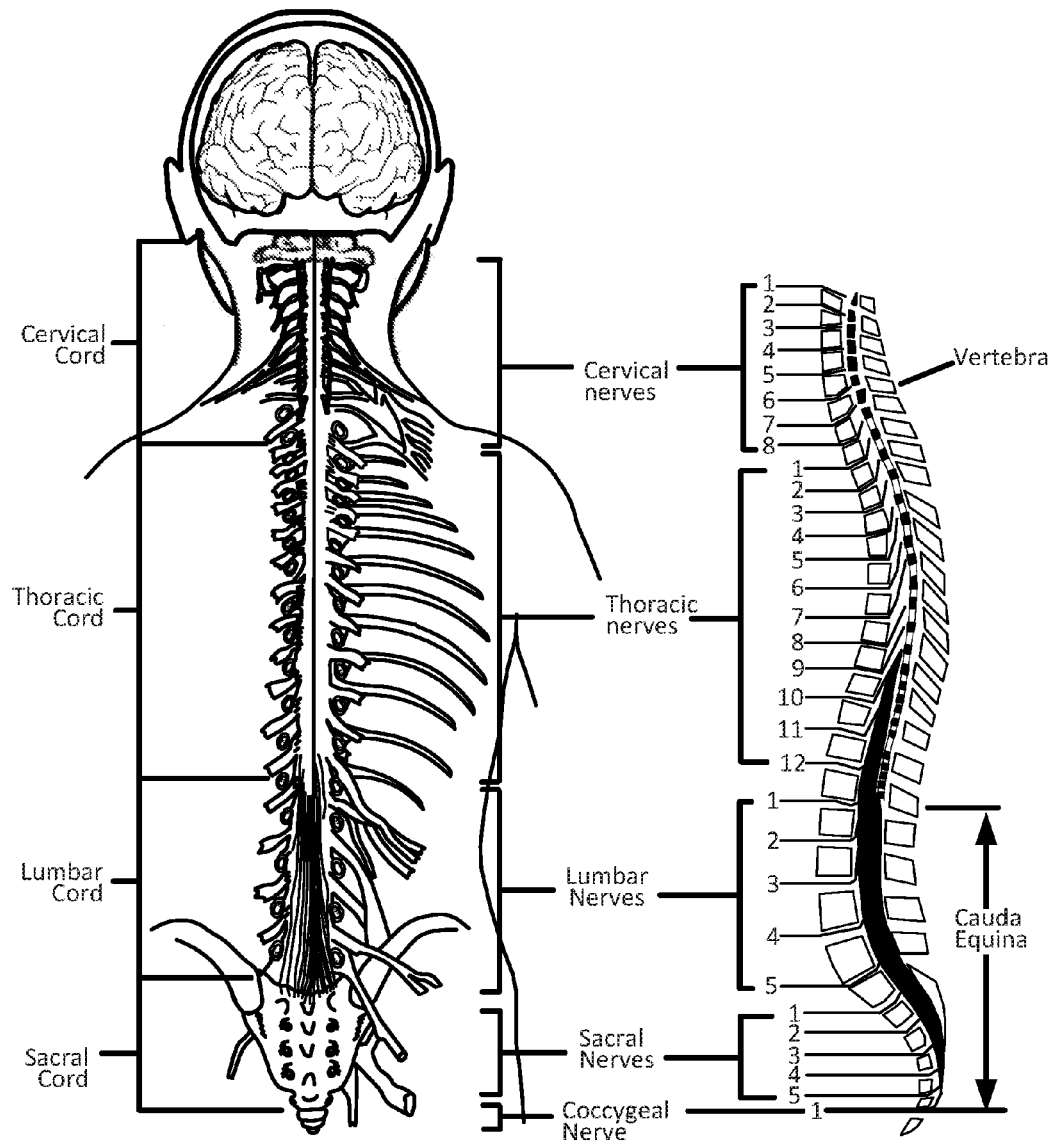
FIGS. 2A-2C show diagrams of the nerve structures along the spine, the lower back and sacrum region, which may be stimulated in accordance with aspects of the invention.
Figure 2B:
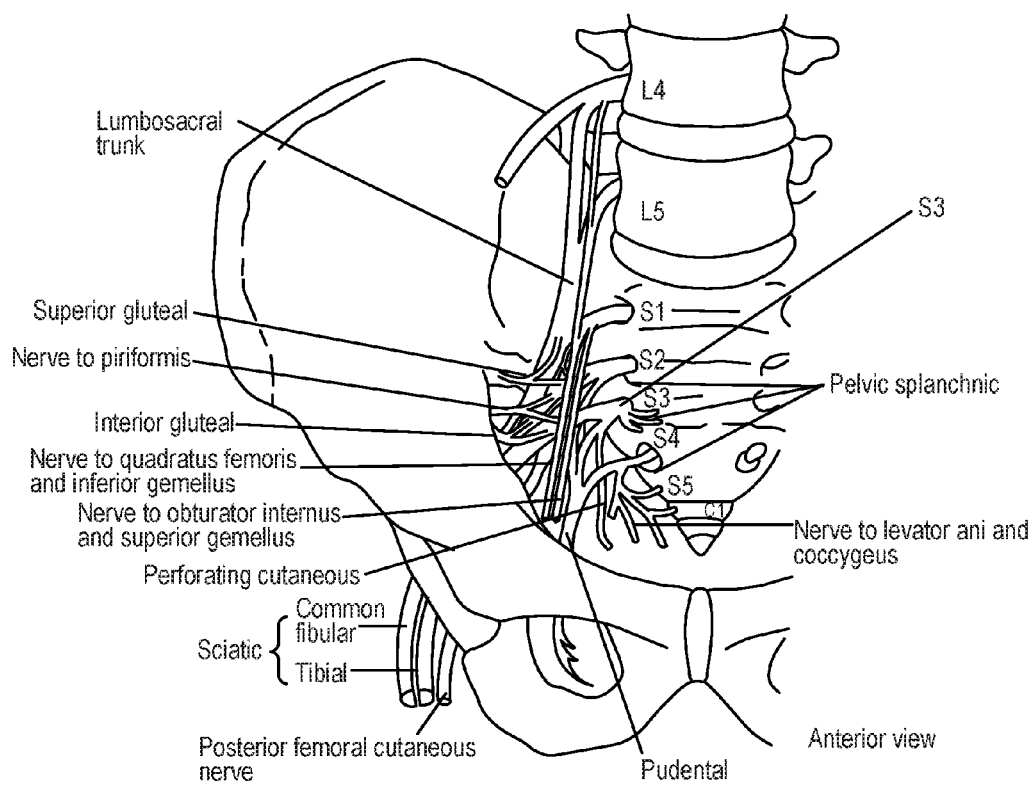
Figure 2C:
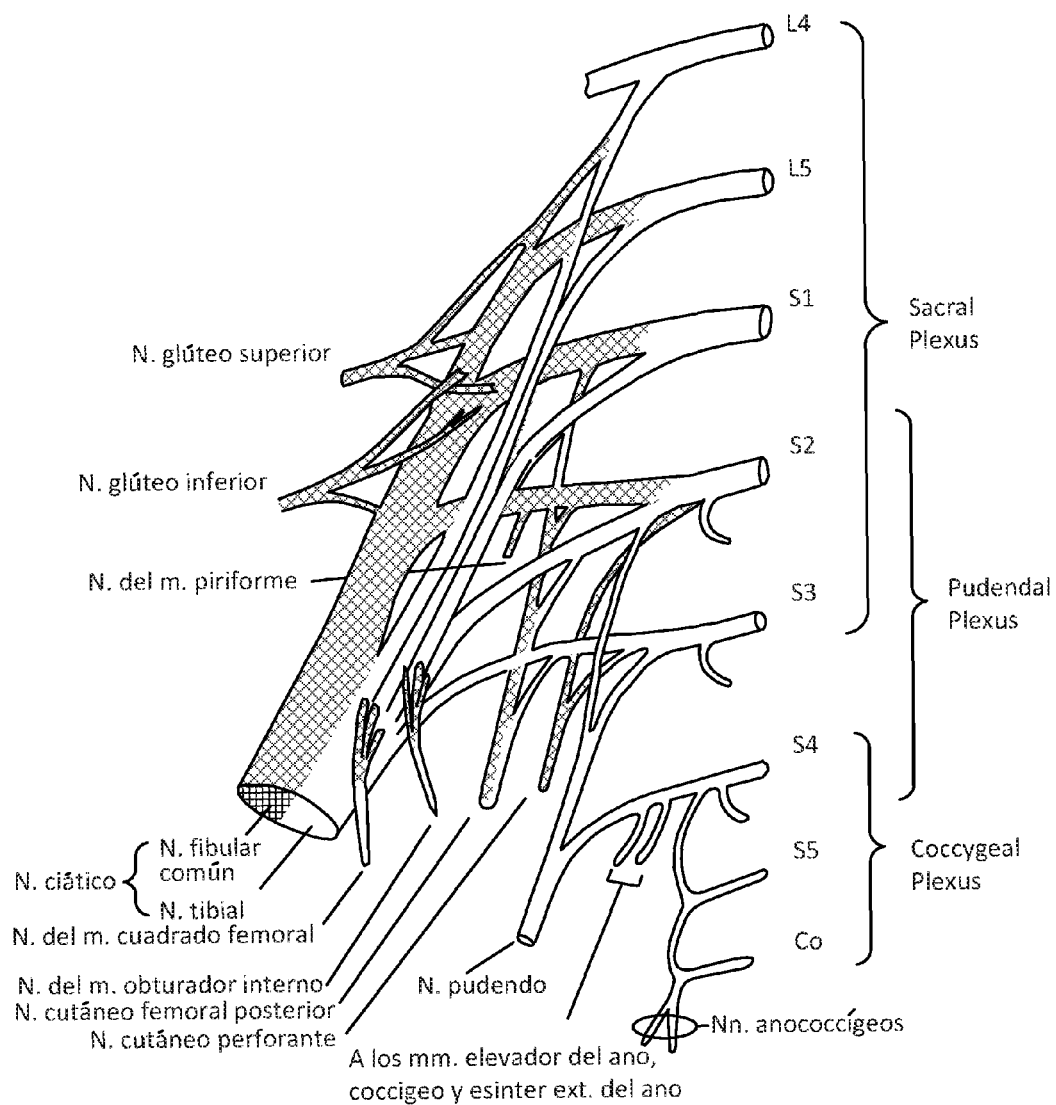

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain threshold may trigger the noted muscle responses, stimulation at a sub-threshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
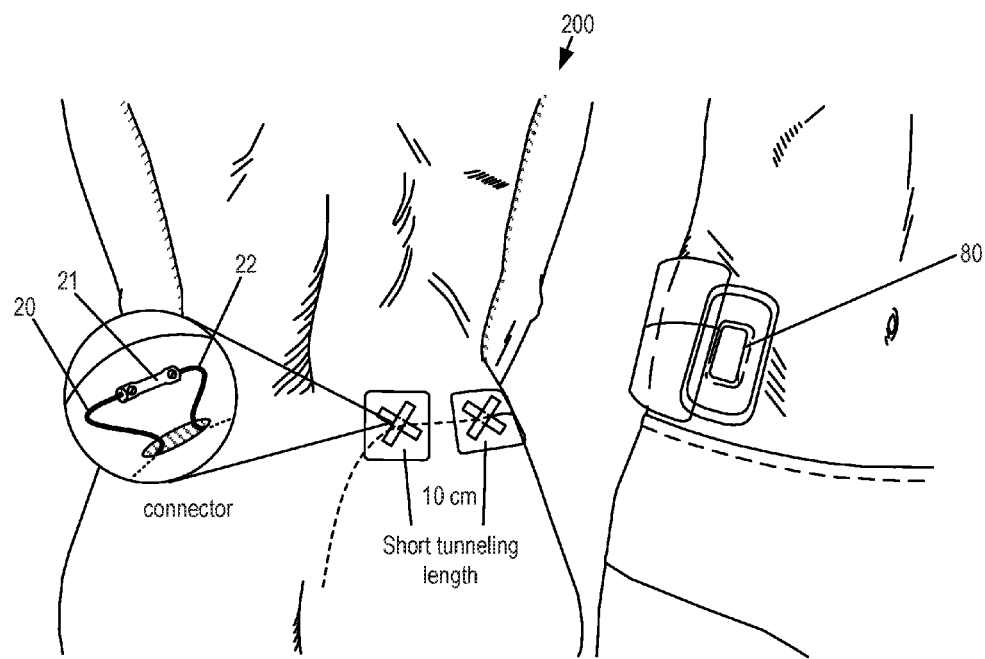
FIG. 3B shows an example of a neurostimulation system having a partly implanted stimulation lead and an external pulse generator adhered to the skin of the patient for use in a trial stimulation, in accordance with aspects of the invention.
Figure 3B:
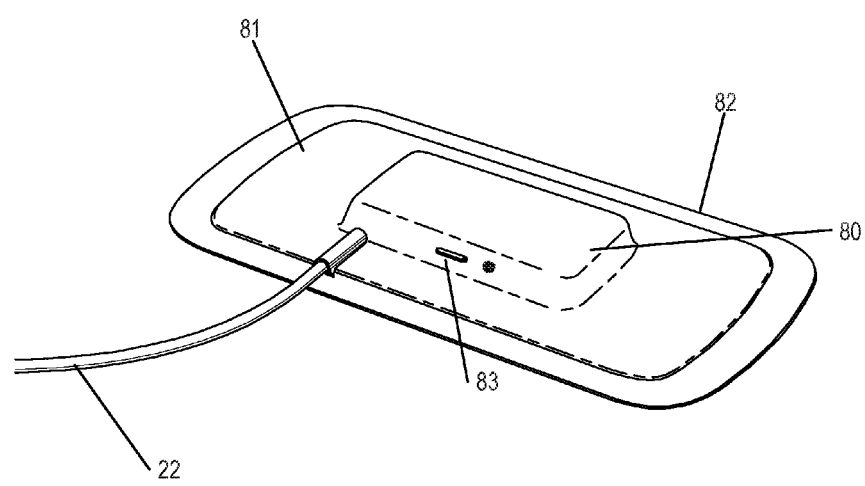

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the clinician programmer using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) there between. This technique may also minimize movement of an implanted lead during conversion of the trial system to a permanently implanted system.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which include an aperture or port through which the EPG 80 is connected to the lead extension 22. The patch may further an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
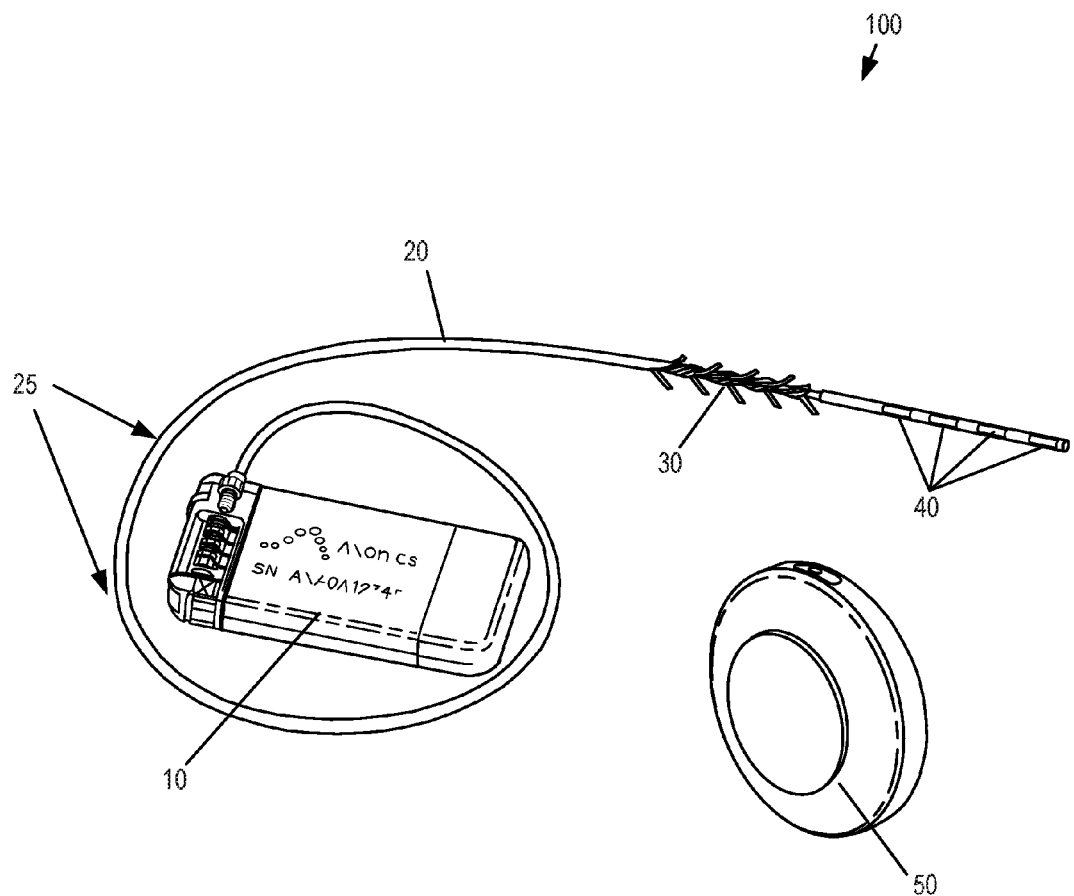
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be either patched to the patient's skin using an adhesive or can be held in place using a belt 53 or by an adhesive patch 52. The CD may be charged by plugging the CD directly into an outlet or by placing the CD in a charging dock or station 51 that connects to an AC wall outlet or other power source.

The system may further include a patient remote 70 and clinician programmer 60, each configured to wirelessly communicate with the implanted IPG, or with the EPG during a trial. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figure 5A:
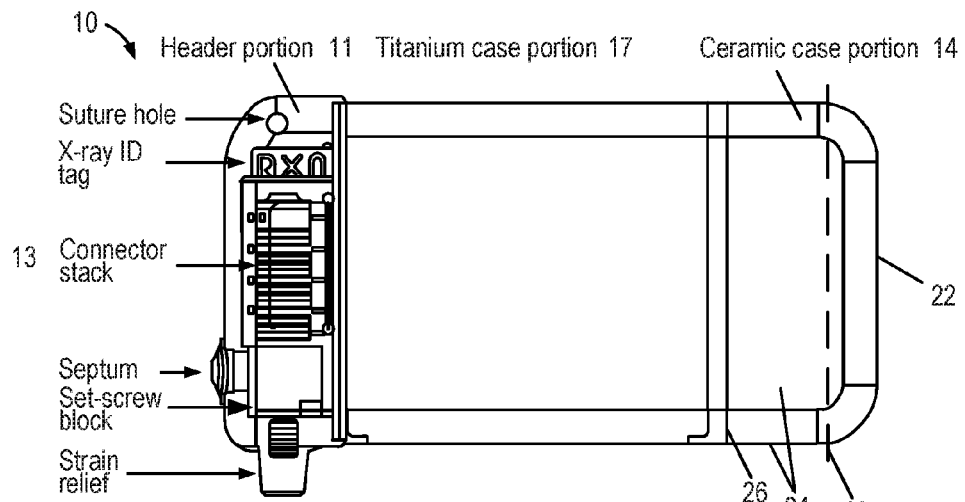
FIG. 5A-5C show detail views of an implantable pulse generator and associated components for use in a neurostimulation system, in accordance with aspects of the invention.
Figure 5B:
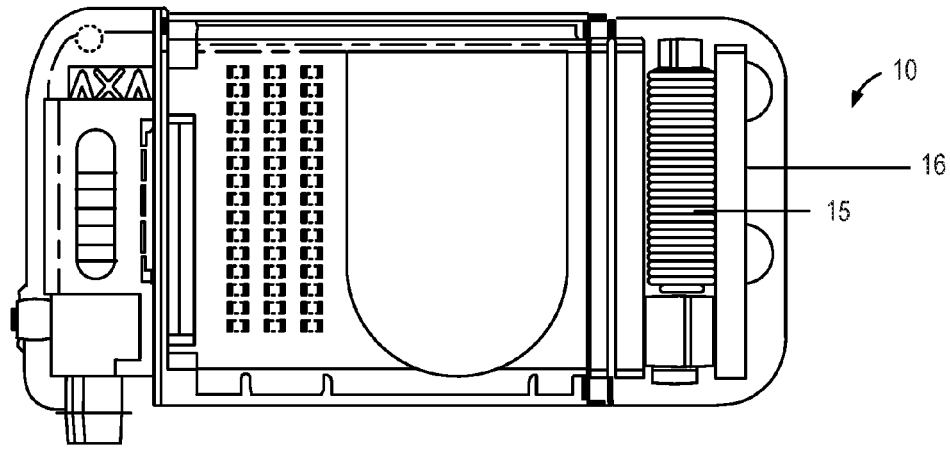
Figure 5C:
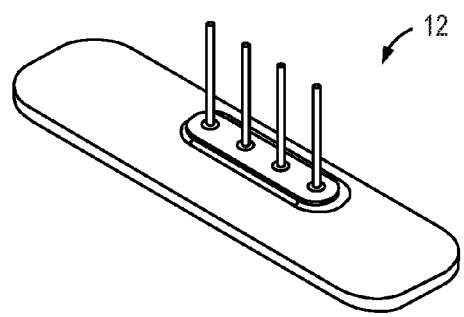

FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 100 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 μs to 500 μs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed through assembly 12 and connector stack 13, while the ceramic case portion 14 houses an antennae assembly 16 to facilitate wireless communication with the clinician program, the patient remote, and/or a charging coil to facilitate wireless charging with the CD. The remainder of the IPG is covered with a titanium case portion 17, which encases the printed circuit board, memory and controller components that facilitate the electrical pulse programs described above. The ceramic portion 14 includes an end 22, sides 24, and a connection portion 26 that connects the ceramic portion 14 to the case portion 17. In the example shown in FIG. 5B, the antennae assembly 16 is positioned such that a plane 28 in which loops of a radiating element lay, is perpendicular to and extends through the sides 24 of the ceramic portion 14.

In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics. In some embodiments, some or all of the pieces of the IPG 10 forming the hermetic housing can be biocompatible, and specifically, can have external surfaces made of biocompatible materials.

In some embodiment, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG, and that ceramic may be used to form additional portions of the case.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at depth of 3 cm with the CD, when positioned on a skin surface of the patient near the IPG and reduces re-charging time.

Figure 6:
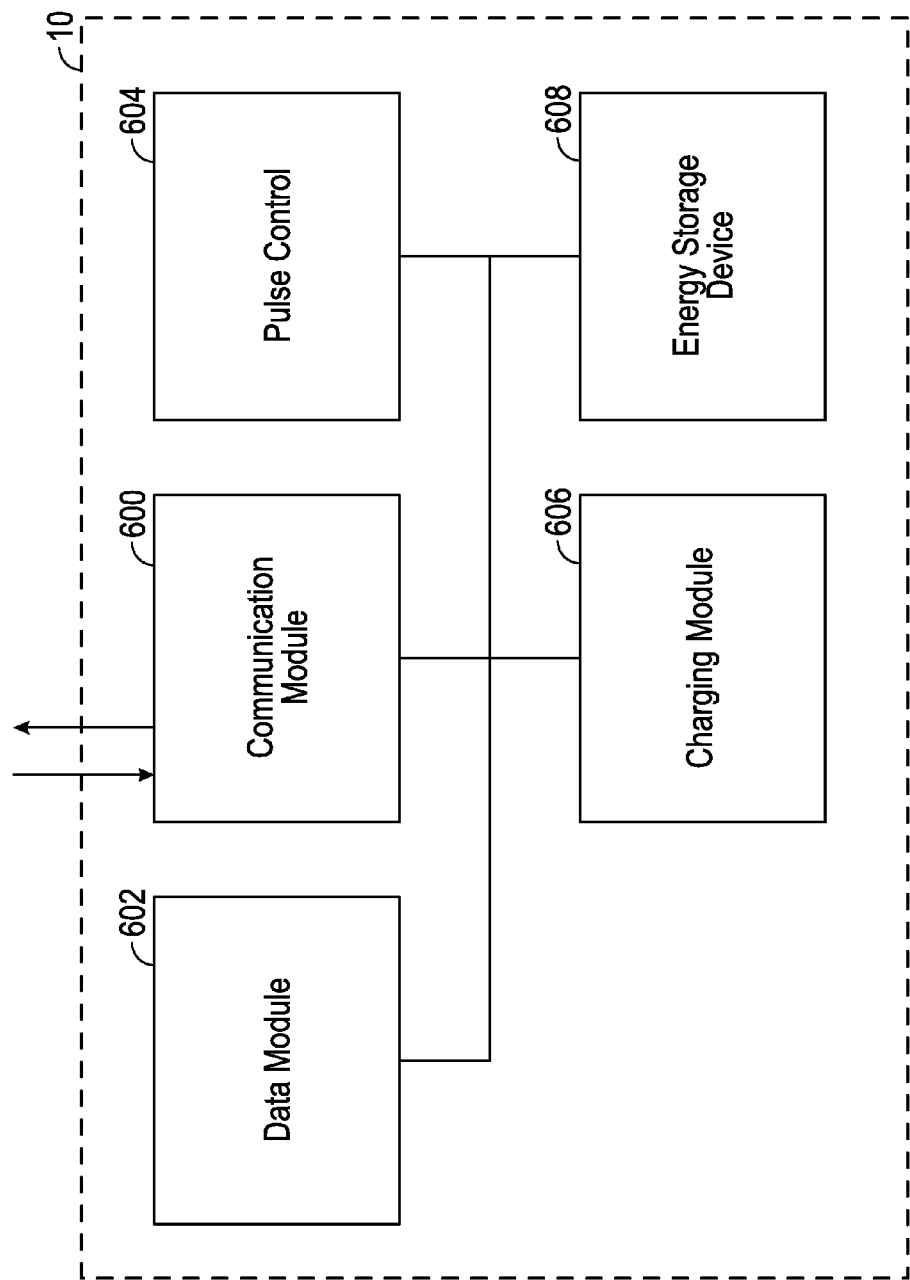
FIG. 6 shows a schematic illustration of one embodiment of the architecture of the IPG.

FIG. 6 shows a schematic illustration of one embodiment of the architecture of the IPG 10 is shown. In some embodiments, each of the components of the architecture of the IPG 10 can be implemented using the processor, memory, and/or other hardware component of the IPG 10. In some embodiments, the components of the architecture of the IPG 10 can include software that interacts with the hardware of the IPG 10 to achieve a desired outcome, and the components of the architecture of the IPG 10 can be located within the housing.

In some embodiments, the IPG 10 can include, for example, a communication module 600. The communication module 600 can be configured to send data to and receive data from other components and/or devices of the exemplary nerve stimulation system including, for example, the clinician programmer 60 and/or the patient remote 70. In some embodiments, the communication module 600 can include one or several antennas and software configured to control the one or several antennas to send information to and receive information from one or several of the other components of the IPG 10. While discussed herein in the context of the IPG 10, in some embodiments, the communication module 600 as disclosed herein can be included in, for example, the charger 116.

The IPG 10 can further include a data module 602. The data module 602 can be configured to manage data relating to the identity and properties of the IPG 10. In some embodiments, the data module can include one or several database that can, for example, include information relating to the IPG 10 such as, for example, the identification of the IPG 10, one or several properties of the IPG 10, or the like. In one embodiment, the data identifying the IPG 10 can include, for example, a serial number of the IPG 10 and/or other identifier of the IPG 10 including, for example, a unique identifier of the IPG 10. In some embodiments, the information associated with the property of the IPG 10 can include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like.

The IPG 10 can include a pulse control 604. In some embodiments, the pulse control 604 can be configured to control the generation of one or several pulses by the IPG 10. In some embodiments, for example, this can be performed based on information that identifies one or several pulse patterns, programs, or the like. This information can further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information can specify aspects of a pulse pattern and/or pulse program, such as, for example, the duration of the pulse pattern and/or pulse program, and/or the like. In some embodiments, information relating to and/or for controlling the pulse generation of the IPG 10 can be stored within the memory.

The IPG 10 can include a charging module 606. In some embodiments, the charging module 606 can be configured to control and/or monitor the charging/recharging of the IPG 10. In some embodiments, for example, the charging module 606 can include one or several features configured to receive energy for recharging the IPG 10 such as, for example, one or several inductive coils/features that can interact with one or several inductive coils/features of the charger 116 to create an inductive coupling to thereby recharge the IPG 10. In some embodiments, the charging module 606 can include hardware and/or software configured to monitor the charging of the IPG 10 including, for example, the charging coil assembly 15.

The IPG 10 can include an energy storage device 608. The energy storage device 608, which can include the energy storage features, can be any device configured to store energy and can include, for example, one or several batteries, capacitors, fuel cells, or the like. In some embodiments, the energy storage device 608 can be configured to receive charging energy from the charging module 606.

Figure 7:
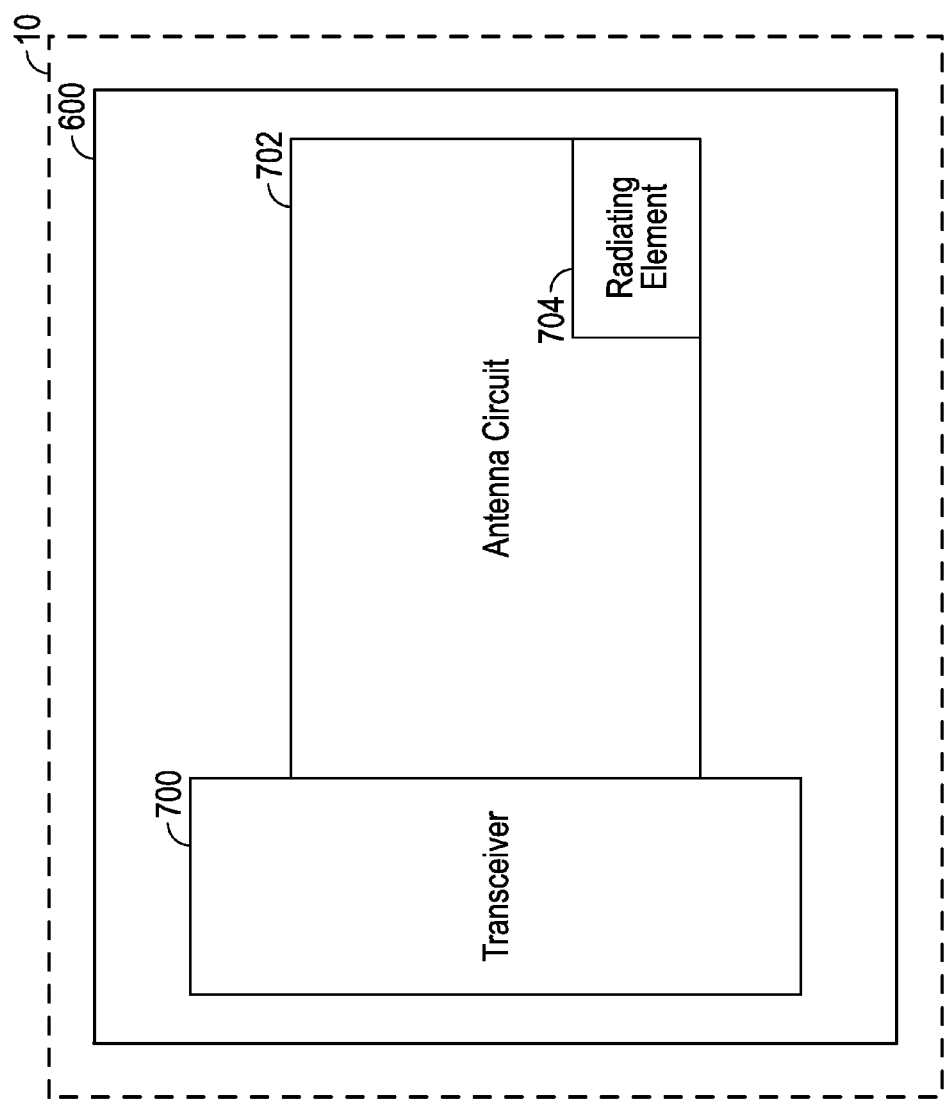
FIG. 7 shows a schematic illustration of one embodiment of the communication module.

FIG. 7 shows a schematic illustration of one embodiment of the communication module 600. The communication module 600 depicted in FIG. 7 includes a transceiver 700 that is connected to an antenna circuit 702, also referred to herein as a "communication antenna circuit," that includes a radiating element 704.

The transceiver 700 can include a transmitter and a receiver that can share common circuitry or a transmitter and receiver that do not share common circuitry. The transceiver 700 can be connected to the antenna circuit 702 so as to transmit data and/or receive data via the antenna circuit 702. In some embodiments in which the charger 116 includes the communication module 600 in addition to the communication module 600 located in the IPG 10, both the communication modules 600 of the charger 116 and of the IPG 10 can include the antenna circuit 702.

The radiating element 704 can comprise a variety of shapes and sizes, and can be made from a variety of materials. In some embodiments, the radiating element 704 can comprise one or several loops of a conductive material such as, for example, copper, that together form an inductive coil. The details of the radiating element 704 will be discussed at greater length below.

Figure 8:
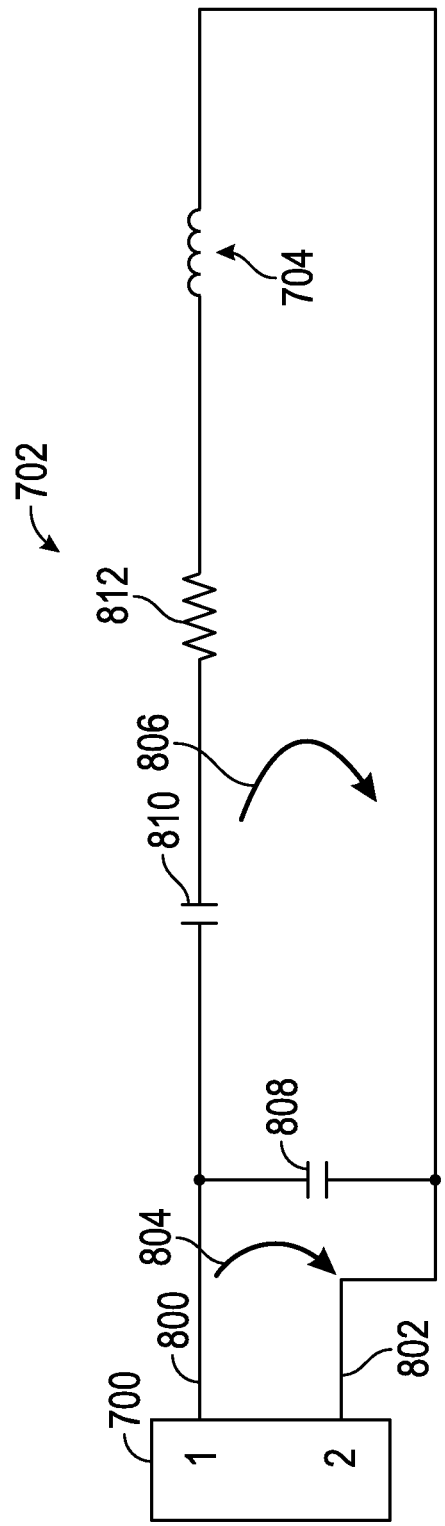
FIG. 8 shows a schematic illustration of the communication module, including a circuit diagram of the antenna circuit.

FIG. 8 shows a schematic illustration of the communication module 600, including a circuit diagram of the antenna circuit 702. As seen in FIG. 8, the transceiver 700 includes a first terminal 800 and a second terminal 802 via which the transceiver 700 is connected to the antenna circuit 702. The antenna circuit 702 includes a first path 804 from the first terminal 800 to the second terminal 802, and a second path 806 from the first terminal 800 to the second terminal 802. As seen in FIG. 8, the first and second paths 804, 806 are parallel paths.

The antenna circuit 702 includes a first capacitor 808, a second capacitor 810, a resistor 812, and the radiating element 704. In some embodiments, one or several of the first capacitor 808, the second capacitor 810, the resistor 812, and the radiating element 704 can be in series or in parallel with the others of the first capacitor 808, the second capacitor 810, the resistor 812, and the radiating element 704. In the embodiment depicted in FIG. 8, the first capacitor 808 is located in the first path 804 and is in parallel with the second capacitor 810, the resistor 812, and the radiating element 704 which are located in the second path 806, and which are in series. In some embodiments, the second capacitor 810, the resistor 812, and the radiating element 704 form an RLC circuit.

In some embodiments, one or both of the first and second capacitor 808, 810 can have a fixed capacitance, and in some embodiments, one or both of the first and second capacitor 808, 810 can have a variable resistance. Similarly, in some embodiments, the resistor 812 can have either a fixed resistance or a variable resistance, and the radiating element 704 can have a fixed or variable inductance.

In some embodiments, the electrical properties of one or several of the first capacitor 808, the second capacitor 810, the resistor 812, and the radiating element 704 can be selected to achieve a desired tuning of the antenna circuit 702. This desired tuning can include, for example, tuning the antenna circuit 702 such that the antenna circuit 702 has a desired resonant frequency, which desired resonant frequency can, for example, correspond to a desired frequency for data transmission, also referred to herein as the "transmission frequency" or the "transmitting frequency." This resonant frequency can be fixed, or variable, and in some embodiments, this resonant frequency can be, for example, between 200 Hz and 600 Hz, between 300 Hz and 500 Hz, between 350 Hz and 450 Hz, approximately 400 Hz, approximately 403 Hz, and/or any other or intermediate value or range. In some embodiments, the resonant frequency can be such that the wavelength of a radio signal generated at the resonant frequency is longer than the longest dimension of the IPG 10. As used herein, "approximately" refers to 1%, 5%, 10%, 15%, 20%, or 25% of the therewith associated value or range.

In some embodiments in which the electrical properties of one or several of the first capacitor 808, the second capacitor 810, the resistor 812, and the radiating element 704 are inconsistent between antenna circuits 702 electrical properties of one or several of the others of the first capacitor 808, the second capacitor 810, the resistor 812, and the radiating element 704 may be adjusted to achieve the desired resonant frequency of the antenna circuit 702. Such adjustment of the electrical properties of one or several of the first capacitor 808, the second capacitor 810, the resistor 812, and the radiating element 704 can occur when the inductance of the radiating elements 704 is not consistent and/or fixed between radiating elements 704. This adjustment of the electrical properties of one or several of the first capacitor 808, the second capacitor 810, and the resistor 812 in response to inconsistent inductance of radiating elements 704 can be time consuming and costly.

In one embodiments, the antenna circuit 702 can be formed on a printed circuit board (PCB), and particularly, the one or several loops of the radiating element can be printed on and/or embedded in the PCB. This embedding of the one or several loops of the radiating element 704 in the PCB can increase the increase the consistency of the inductance of the radiating elements 704 across several antenna circuits 702. This consistency in the inductance across several radiating elements 704 can allow the use of first and second capacitors 808, 810 having fixed capacitance and resistor 812 having a fixed resistance in the creation of the antenna circuit 702 and can eliminate the need for tuning of the antenna circuit via the adjustment of the electrical properties of one or several of the first capacitor 808, the second capacitor 810, and the resistor 812.

In some embodiments, the antenna circuit 702 can be further tuned such that the antenna circuit 702 has a desired bandwidth. The bandwidth of the antenna circuit can be determined with a variety of known techniques, and in some embodiments can be defined as the range of frequencies within which the performance of the antenna, with respect to some characteristic, conforms to a specified standard, and specifically the range of frequencies over which the output power of the antenna circuit is greater than the half-power point, and thus is greater than one-half of the mid-band value. In some embodiments, the antenna circuit 702 can be tuned to have a desired bandwidth by the inclusion of resistor 812 in the antenna circuit 702, and specifically by inclusion of resistor 812 have a desired resistance level in the antenna circuit 702.

In some embodiments, the inclusion of resistor 812 can decrease the Q factor of the antenna circuit 702, and can thus decrease the mid-band value of the antenna circuit 702. However, this disadvantageous decrease in the Q factor can be offset by the benefit of the increased bandwidth of the antenna circuit 702. Specifically, the implantation of the antenna circuit 702 into the body of the patient can affect resonant frequency of the antenna circuit 702. Thus, the antenna circuit 702 can have a first resonant frequency when not implanted in a patient's body, and a second resonant frequency when implanted in the patient's body. Further, this second resonant frequency is not consistent between patients, but rather varies based on one or several properties of the tissue into which the antenna circuit 702, including the antenna circuit 702 in the IPG 10, is implanted. These properties of the tissue can include, for example, at least one of a density, a hydration level, a resistance, an inductance, and a tissue type.

While this effect of the implantation of the antenna circuit 702 on the resonant frequency varies from patient to patient, the bandwidth of the antenna circuit 702 can be tuned to include a large percentage of the expected second frequencies of the antenna circuit 702. In some embodiments, this bandwidth can be, for example, between 1 Hz and 50 Hz, between 5 Hz and 30 Hz, between 10 Hz and 20 Hz, approximately 20 Hz, approximately 16 Hz, and/or any other or intermediate value or range. Thus, in such embodiments, the effectiveness of the antenna circuit 702 at receiving the transmitting frequency does not drop below the half-power point when the antenna circuit 702 is implanted into a patient's body.

Figure 9A:
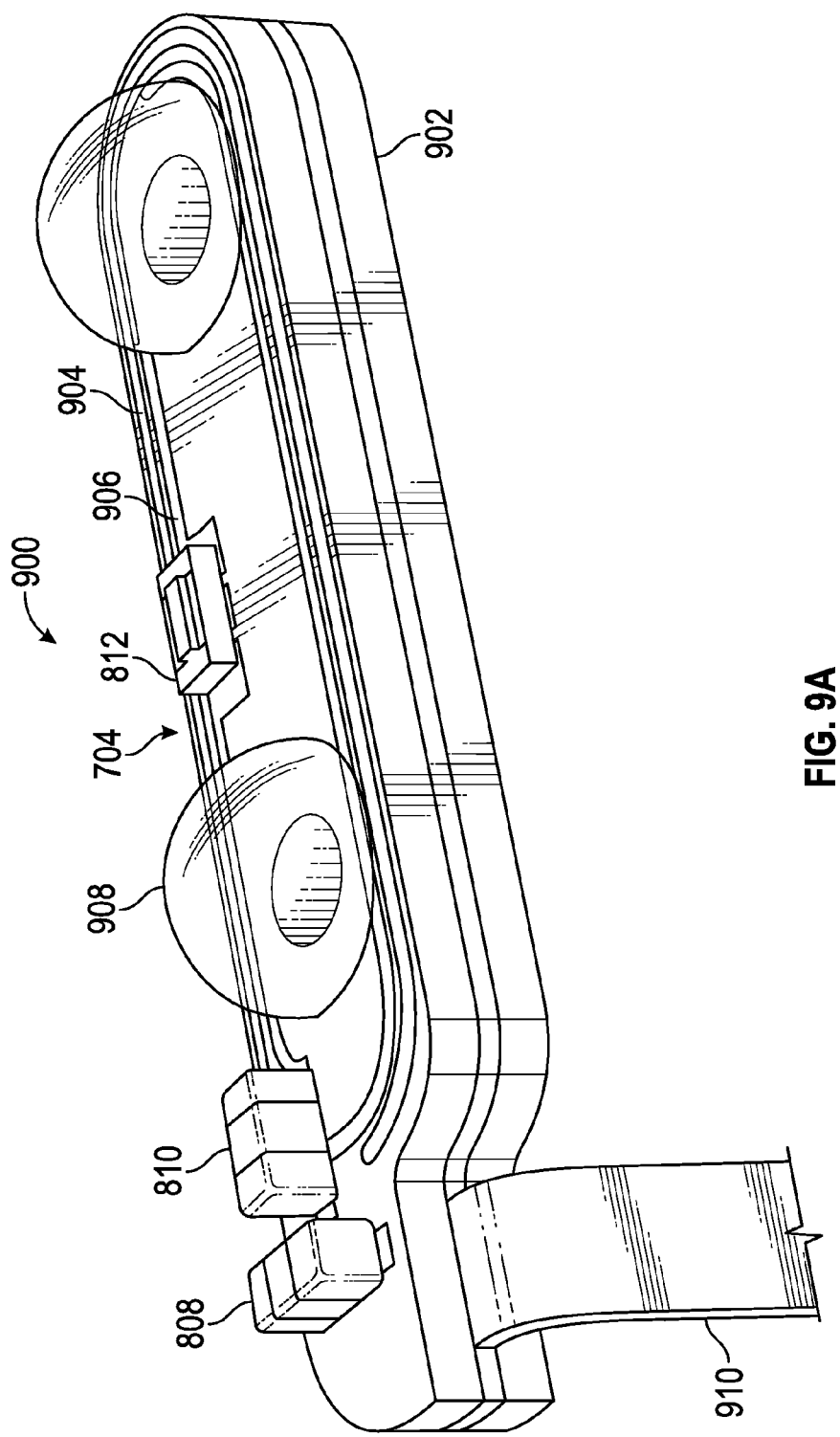
FIG. 9A shows a perspective view of one embodiment of an antenna assembly.
Figure 9B:
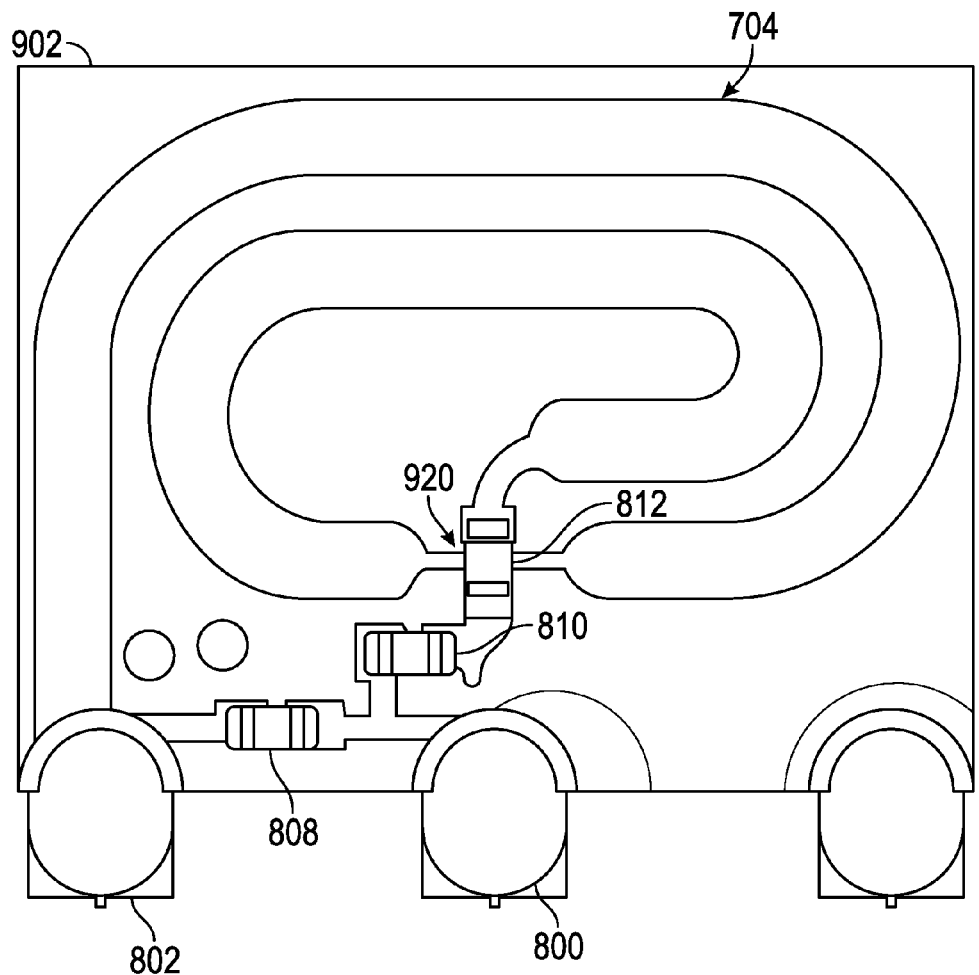
FIG. 9B shows a top view of one embodiment of the antenna assembly.

FIG. 9A shows a perspective view of one embodiment of an antenna assembly 900 and FIG. 9B shows a top view of one embodiment of the antenna assembly 900. The antenna assembly can be used in the communication module 600 of one or both the IPG 10 and the charger 116. In some embodiments, both the IPG 10 and the charger 116 can include the antenna assembly 900. The antenna assembly 900 includes a printed circuit board (PCB) 902 upon which the first and second capacitors 808, 810 and the first resistor 812 are mounted, and in which the radiating element 704 is embedded.

As specifically seen in FIGS. 9A and 9B, the radiating element 704 comprises a plurality of loops, and specifically, a first loop 904 and a second loop 906. In some embodiments, the radiating element can comprise a single copper trace formed and/or embedded in the PCB 902, which single copper trace is shaped to create the first loop 904 and the second loop 906. In some embodiments, the first and second loops 904, 906 can each comprise a copper trace formed and/or embedded in the PCB 902. In some embodiments, the first and second loops 904, 906 can be located in the same plane within the PCB 902. In some embodiments, placement of the first and second loops 904, 906 in the same plane within the PCB 902 can be enabled by the placement of one of the loops 904, 906 within the other of the loops 904, 906, and as shown in FIG. 9A, by the placement of the second loop 906 within the first loop 904.

In some embodiments, the antenna assembly 900 can further include one or several spacers 908 and/or bumpers that can facilitate in properly positioning the antenna assembly 900 within the IPG 10 and a connector, such as a flex-connector 910 that can be used to electrically connect the antenna assembly 900 to other components of the IPG 10 such as, for example, the transceiver 700.

In some embodiments, and as seen in FIG. 9B, the radiating element 704 can include a necked down portion 920. The necked down portion 920 of the radiating element 704 can pass the resistor 812 without electrically connecting to the resistor 812. In some embodiments, the necked down portion 920 can be located relatively deeper in the PCB 902 than the resistor 812. In some embodiments, the necked down portion 920 and the other portions of the radiating element 704 can be located at the same depth in the PCB 902, in a common plane that is relatively deeper than the resistor 812.

Figure 10:
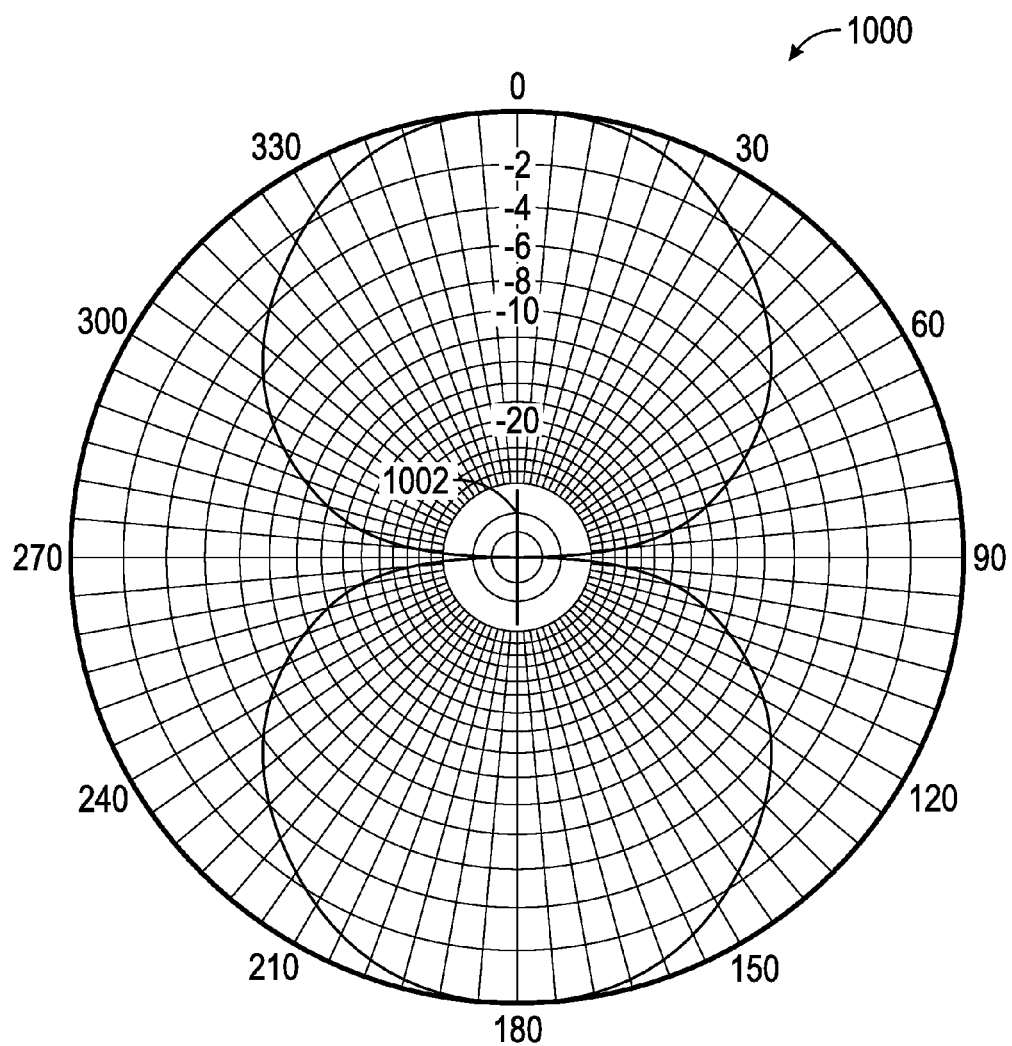
FIG. 10 shows a depiction of the electric field dipole pattern created by the antenna assembly depicted in FIGS. 9A and 9B.

FIG. 10 shows a depiction of the electric field dipole pattern 1000 created by the antenna assembly 900 depicted in FIGS. 9A and 9B. The electric field dipole pattern 1000 is a donut pattern with the maximum strength in the plane 1002 of the first and second loops 904, 906, with the electric field polarization in the plane 1002 of the first and second loops 904, 906 (parallel to the current flow in the wire loop). With the IPG 10 placed flat in the patient's body such that the header portion 11 and the ceramic case 14 are equidistant from the body surface or such that the plane 1002 of the first and second loops 904, 906 is perpendicular to the body surface, the maximum field is normal to the body surface (outward) to achieve the best communication reliability possible.

Figure 11:
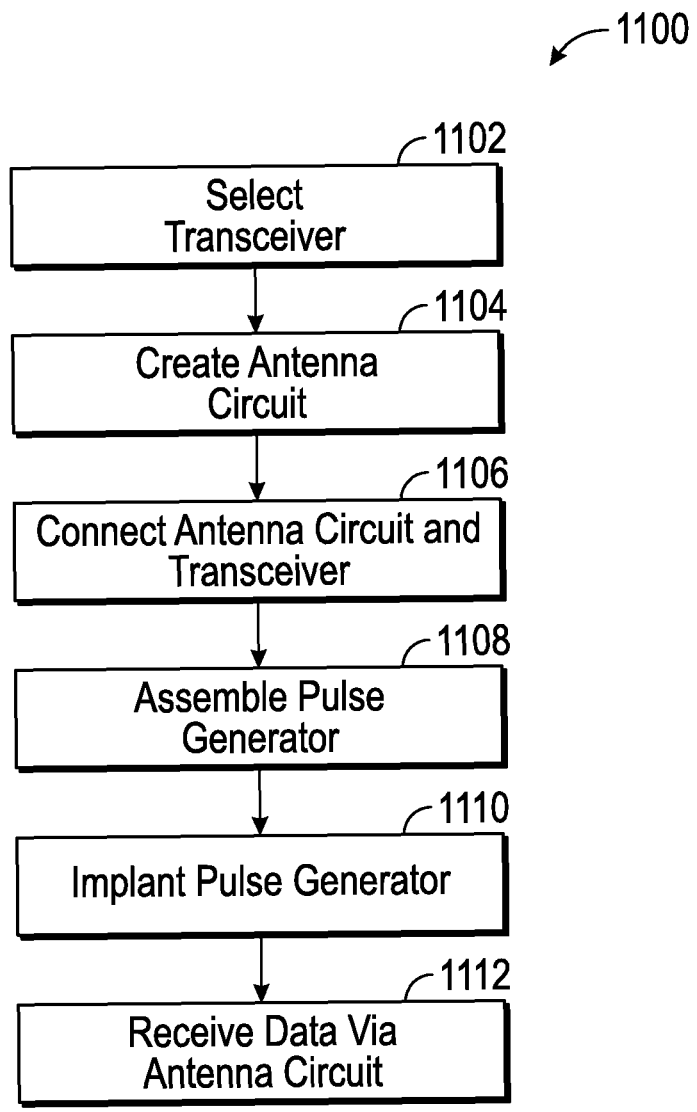
FIG. 11 is a flowchart illustrating one embodiment of a process for manufacturing a communication module and for wireless communication of data between an implantable neurostimulator and an external device.

FIG. 11 is a flowchart illustrating one embodiment of a process 1100 for manufacturing a communication module and for wireless communication of data between an implantable neurostimulator and an external device. The process 1100 begins at block 1102, wherein a transceiver is selected. In some embodiments, the transceiver can be selected according to one or several desired parameters such as, for example, power consumption, output power, broadcast/receive frequencies, and/or the like. In some embodiments, the selection of a transceiver can correspond to the retrieval of a transceiver for assembly with an antenna circuit.

After the transceiver has been selected, the process 1100 proceeds to block 1104, wherein the antenna circuit is created. In some embodiments, this can include the creation of the PCB, including the embedding of the copper traces of the radiating element in the PCB, the attaching of the capacitors and/or resistors to the PCB, and the attaching of one or several connectors to the PCB. In some embodiments, the creation of the antenna circuit can further include the tuning of the antenna circuit, and specifically, the tuning of the bandwidth of the antenna circuit to encompass frequency shifts arising from the implantation of the antenna circuit into the body of the patient. In some embodiments, this bandwidth can be selected based on data gathered from one or several patients that is indicative of the statistical distribution of the frequency shifts arising from the implantation of the antenna circuit in the patient's body, and the selection of a bandwidth that will encompass all, or some percentage of the statistical distribution. In some embodiments, this percentage can include, for example, at least 50 percent of the statistical distribution, at least 60 percent of the statistical distribution, at least 70 percent of the statistical distribution, at least 80 percent of the statistical distribution, at least 90 percent of the statistical distribution, at least 95 percent of the statistical distribution, at least 97 percent of the statistical distribution, at least 98 percent of the statistical distribution, at least 99 percent of the statistical distribution, at least 99.5 percent of the statistical distribution, at least 99.9 percent of the statistical distribution, and/or any other or intermediate percent of the statistical distribution.

After the antenna circuit has been created, the process 1100 proceeds to block 1106, wherein the antenna circuit is connected to the transceiver. In some embodiments, this can include the connection of the first and second terminals of the transceiver to portions of the antenna circuit, such as is depicted in, for example, FIG. 8. In some embodiments, the transceiver can be connected to the antenna circuit via a flex connector, or via any other electrical connection.

After the antenna circuit has been connected to the transceiver, the process 1100 proceeds to block 1108, wherein the pulse generator is assembled. In some embodiments, this can include the assembly of the IPG 10, and can include the connection of the communication module, and specifically the connected transceiver and antenna circuit to one or several other components of the pulse generator.

After the pulse generator has been assembled, the process 1100 proceeds to block 1110, wherein the pulse generator is implanted. After the pulse generator has been implanted, the process 1100 proceeds to block 1112, wherein data is received at the pulse generator from the external device via the communications module, and specifically via the antenna circuit and the transceiver. In some embodiments, this data can be received at the transmission frequency, which transmission frequency can be within the bandwidth of the antenna circuit at one or both of the first and second resonant frequencies. In some embodiments, this data can be used to control and/or modify control of the pulse generator. Further, in some embodiments, the receiving of data via the antenna circuit can further include the transmission of data via the transceiver and the antenna circuit.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An implantable neurostimulator for delivering one or more electrical pulses to a target region within a patient's body according to a program received via wireless communication with an external device, the implantable neurostimulator comprising:
a hermetic housing having a biocompatible external surface and that is configured to be implanted within a body of a patient;
a transceiver disposed within the hermetic housing and comprising a first lead and a second lead; and
a communication antenna circuit defined by a Q factor and disposed within the hermetic housing, the communication antenna circuit coupled to the first lead and the second lead, the communication antenna circuit having a first path and a second path parallel to the first path, the first path comprising a first capacitor, and the second path comprising:
a second capacitor;
a radiating element; and
a resistor, wherein the second capacitor, the resistor, and the radiating element are arranged in series, and wherein the Q factor of the communication antenna circuit is limited at a resonant frequency by the resistor.

2. The implantable neurostimulator of claim 1, wherein the communication antenna circuit comprises a printed circuit board (PCB).

3. The implantable neurostimulator of claim 2, wherein the radiating element comprises a plurality of conductive loops on the PCB, and wherein the plurality of conductive loops are located along a common plane of the PCB.

4. The implantable neurostimulator of claim 3, wherein the conductive loops comprise copper traces embedded onto a substrate surface of the PCB, and wherein the copper traces are configured to produce an electric field dipole having a donut pattern with a maximum strength in the common plane such that a maximum field is substantially normal to a body surface of the patient when the hermetic housing is implanted for use.

5. The implantable neurostimulator of claim 4, wherein the plurality of conductive loops comprises a first loop and a second loop, wherein the second loop is located within the first loop.

6. The implantable neurostimulator of claim 5, wherein the communication antenna circuit has a fixed resonant frequency, the first capacitor has a first fixed capacitance and the second capacitor has a second fixed capacitance.

7. The implantable neurostimulator of claim 6, wherein the fixed resonant frequency corresponds to a transmitting frequency at which the implantable neurostimulator is configured to receive one or more wireless communications.

8. The implantable neurostimulator of claim 6, wherein the resistor is configured to diminish the Q factor of the communication antenna circuit such that a bandwidth of the communication antenna circuits encompasses patient implantation-related variability in resonant frequency when the communication antenna circuit is implanted in the patient body and communicates with the external device.

9. The implantable neurostimulator of claim 6, wherein the communication antenna circuit has a bandwidth, wherein the bandwidth of the communication antenna circuit is tuned such that an effectiveness of the communication antenna circuit at receiving a transmitting frequency does not drop below a half-power point of the communication antenna circuit when implanted within the body of the patient.

10. The implantable neurostimulator of claim 1, wherein the hermetic housing comprises at least a ceramic case portion so as to provide an efficient radio frequency transparent window for wireless communication between the implantable neurostimulator and the external device, wherein the external device comprises a clinician programmer, patient remote, or a charging device.

11. The implantable neurostimulator of claim 1, further comprising a charging coil assembly comprising a ferritic core located adjacent to the communication antenna circuit within the hermetic housing.

12. A method of wireless communication of data between an implantable neurostimulator and an external device, the method comprising:
implanting the neurostimulator in a patient's body, the implantable neurostimulator comprising:

a hermetic housing;

a transceiver disposed within the hermetic housing and comprising a first lead and a second lead; and an antenna circuit disposed within the hermetic housing and coupleable to the first lead and the second lead, the antenna circuit having a first path and a second path parallel to the first path, the first path comprising a first capacitor, and the second path comprising:

a second capacitor;

a radiating element; and a resistor, wherein the second capacitor, the resistor, and the radiating element are arranged in series, wherein the antenna circuit has a resonant frequency, and wherein a Q factor of the antenna circuit is limited at the resonant frequency by the; and receiving data wirelessly transmitted from the external device at the implantable neurostimulator, wherein the data is transmitted at a transmission frequency and is configured to control delivery of one or more electrical pulses to a target region within the patient's body.

13. The method of claim 12, wherein the resonant frequency is a fixed resonant frequency, and wherein the first capacitor has a first fixed capacitance and the second capacitor has a second fixed capacitance.

14. The method of claim 12, wherein implanting the neurostimulator into the patient's body creates an effective resonant frequency of the antenna circuit, the effective resonant frequency differing from the resonant frequency in response to one or more properties of a tissue of the patient's body into which the neurostimulator is implanted.

15. The method of claim 14, wherein the one or more properties of the tissue of the patient's body comprise at least one of: a density, a hydration level, a resistance, an inductance, or a tissue type.

16. The method of claim 15, wherein the antenna circuit is tuned to have a bandwidth encompassing both the effective resonant frequency and the transmission frequency.

17. The method of claim 16, wherein the antenna circuit comprises a printed circuit board (PCB).

18. The method of claim 17, wherein the radiating element comprises a plurality of conductive loops formed on the PCB.

19. The method of claim 18, wherein the plurality of conductive loops comprises a first loop, and second loop, wherein the second loop is located within the first loop.

20. The method of claim 19, wherein the conductive loops comprise copper traces embedded onto a substrate surface of the PCB along a common plane of the PCB, and wherein the copper traces are configured to produce an electric field dipole having a donut pattern with a maximum strength in the common plane such that a maximum field is substantially normal to a body surface of the patient after the implanting of the neurostimulator.

* * * * *